United States Patent [19]

Rawlins

[11] Patent Number: 4,719,228

[45] Date of Patent: Jan. 12, 1988

[54] PHARMACEUTICAL COMPOSITION

[75] Inventor: David A. Rawlins, 23 Harwood Close, Tewin, Hertfordshire, England

[73] Assignee: David A. Rawlins, Hertfordshire, England

[21] Appl. No.: 736,337

[22] Filed: May 21, 1985

[30] Foreign Application Priority Data

May 23, 1984 [GB] United Kingdom ............... 8413191

[51] Int. Cl.$^4$ ...................... A61K 31/35; A61K 47/00
[52] U.S. Cl. .................................... 514/456; 514/770; 514/951; 514/960; 514/962; 424/451; 424/464
[58] Field of Search ............... 514/424, 453, 769, 770, 514/948, 951, 456, 962; 424/23, 154, 464, 451

[56] References Cited

U.S. PATENT DOCUMENTS 4,254,099 3/1981 Asmussen et al. .................... 424/23

FOREIGN PATENT DOCUMENTS 2107706 5/1983 United Kingdom ............... 514/453

Primary Examiner—J. R. Brown
Assistant Examiner—John W. Rollins
Attorney, Agent, or Firm—Hopgood, Calimafde, Kalil, Blaustein & Judlowe

[57] ABSTRACT

A pharmaceutical composition comprising a freely flowable powder, the powder comprising a porous, high absorption silica or silicate having absorbed therein at least 10% by volume of a liquid, pharmaceutically active composition, based on the weight of powder plus liquid, provided that when the liquid pharmaceutically active composition is a corticoid solution the silica or silicate has a mean particle size of at least 10 $\mu$m in diameter.

12 Claims, No Drawings

PHARMACEUTICAL COMPOSITION

The present invention relates to a pharmaceutical composition, and in particular to a composition in which the active ingredient is incorporated into a freely-flowable powder.

Hitherto, certain synthetic silicas have been used to absorb liquid pesticides, such as malathion, diazinon and parathion, to form freely-flowable powder concentrates which have good storage stability. Such silicas have also been used in a similar way to absorb liquid animal feed additives, such as ethoxyquin, molasses and choline chloride.

In addition corticoid solutions have been dispersed on amorphous porous silicas of small particle size (J.Pharm.Sci. 1984, 73 401–403).

It has now been found that silicas can be used to absorb liquid pharmaceutical compositions to form freely-flowable powder concentrates which, when administered in unit dose formulations, can provide more rapid and complete drug release than conventional drug containing formulations. This is of particular value for drugs, such as digoxin or phenytoin, where bioavailability problems exist.

According to the present invention there is provided a pharmaceutical composition comprising a freely-flowable powder, the powder comprising a porous, high absorption silica or silicate having absorbed therein at least 10% by volume of a liquid, pharmaceutically active composition, based on the weight of powder plus liquid, provided that when the liquid pharmaceutically active composition is a corticoid solution, the silica or silicate has a mean particle size of at least 10 μm in diameter.

Examples of useful silicas are precipitated silicas or xerogels. Examples of useful silicates are aluminosilicates or calcium silicates.

The silicas or silicates preferably have a liquid absorption capacity of from 100 to 300 mls per 100 g. of silica or silicate, as determined by the ASTM D281 or DIN 53199 methods. Preferred silicas are those marketed by Degussa under the Sipernat and Wessalon trade marks.

The preferred percentage by volume of liquid is from 30% to 75%, more preferably 40% to 75% v/w.

The silicas or silicates suitably have a mean particle size of at least 10 μm in diameter. Preferably the particle size is within the range of 10 μm to 1 mm in diameter.

Suitably the composition is in unit dosage form. Examples of unit dose formulations of the present invention include capsule and tablet formulations, preferably a capsule formulation.

Preferably for capsule formulations, the silicas or silicates may have a mean particle size within the range of 20 μm to 1 mm in diameter. A particularly preferred mean particle size is within the range of 30 μm to 500 μm in diameter.

Preferably for tablet formulations, the silicas or silicates may have a mean particle size within the 10 μm to 500 μm. A particularly preferred mean particle size is within the range of 50 μm to 500 μm in diameter more particularly of 150 μm to 250 μm in diameter.

The liquid, pharmaceutically active composition preferably comprises a pharmaceutically active ingredient in a liquid diluent or carrier. The active ingredient may be dissolved or dispersed in the liquid diluent or carrier, which may be a water miscible or water immiscible medium.

Examples of liquid diluents or carriers include the following three classes:

(a) Water miscible carriers
Propylene Glycol
Polyethylene Glycol
Water
Solketal
Glycofurol
Dimethylisosorbide
Nonionic surface active agents (b) Oils and Organic carriers
Fractionated Coconut Oil
Sesame Oil
Soya Bean Oil
Liquid Paraffin
Isopropylmyristate
Triacetin (c) Semi-solid carriers
High molecular weight polyethylene glycols
White soft paraffin Examples of pharmaceutically active ingredients include anti-hypertensive agents, anti-inflammatory agents, tranquilisers, cardiotonic agents, antibacterial agents, antidepressants, corticosteroids, anti-ulcer agents, anti-allergy agents and anti-obesity agents.

The above described compositions are particularly useful when the pharmaceutically active ingredients have poor aqueous solubility and bioavailability problems, such as diazepam and digoxin.

A preferred class of pharmaceutically active ingredients are anti-hypertensive agents in particular those described in European Published Patent Application No. 0076075, such as 6-cyano-3, 4-dihydro-2,2-dimethyl-trans-4-(2-oxo-1-pyrrolidinyl)-2H-benzo-[b]pyran-3-ol.

It has been found advantageous to dissolve these ingredients in a water miscible carrier, for example solketal or glycofurol, for absorption into a silica or silicate.

The freely flowable powder may be made by admixture of the liquid pharmaceutically active composition with the silica or silicate, with subsequent agitation to obtain homogeneous distribution of the composition in the silica or silicate.

The liquid pharmaceutically active composition may be made in a conventional manner, by admixture of a pharmaceutically active ingredient with a suitable liquid diluent or carrier.

In the case where the liquid diluent or carrier is a semi-solid material, formation of the freely flowable powder is conveniently carried out by heating together a mixture of silica or silicate and the semi-solid above the melting point of the semi-solid, and shaking the resulting mixture.

Tablets and capsules for administration may contain conventional excipients such as binding agents, acacia, gelatin, sorbitol, tragacanth, or polyvinylpyrrolidone: fillers, for example lactose, sugar, maize-starch, calcium phosphate, sorbitol or glycine; tabletting lubricants, for example magnesium stearate, talc, polyethylene glycol or silica; disintegrants, for example potato starch or cross-linked polyvinyl pyrrolidone; acceptable wetting agents such as sodium lauryl sulphate; and conventional flavouring or colouring agents.

Preferably the tablet or capsule formulation comprises greater than 30% w/w of the freely flowable silica or silicate.

Capsule formulations of the invention may be made in conventional manner, by filling the freely flowable powder into a capsule shell.

Tablet formulations of the invention may be made in conventional manner, by compacting the freely flowable powder, if necessary in the presence of a conventional excipient such as those described above.

The following Examples illustrate the invention.

EXAMPLE 1

INDOMETHACIN CAPSULES

A 25% w/v solution of Indomethacin was prepared in each of the following carriers.

(a) Glycofurol
(b) Dimethylisosorbide
(c) 25% Synperonic 8* in Dimethylisosorbide

* Synperonic 8 is a non-ionic surfactant manufactured by I.C.I.

5.5 ml of each solution was mixed with 3.7 grams of silica (Sipernat 50) to give a c.60% liquid inclusion level. 1.15 grams of cross-linked polyvinylpyrrolidone was added as a disintegrant. Sufficient quantity of this mix was filled into a clear No. 2 hard gelatin capsule to give a drug content of 25 mg.

EXAMPLE 2

KETAZOLAM CAPSULES 1.50 g of ketazolam was dispersed in a 25% Tween 80-Solketal or dimethylisosorbide solution to a volume of 11 ml and allowed to equilibrate for four hours.

5.5 ml of the dispersion was mixed with 3.70 grams of silica (Sipernat 50). 1.15 grams of cross linked polyvinylpyrrolidone was added as a disintegrant. 221 mg of this mix was filled into a clear No. 2 hard gelatin capsule being equivalent to a ketazolam content of 15 mg.

EXAMPLE 3

DIAZEPAM CAPSULES

A 9.1% w/v solution of diazepam in solketal was prepared. 5.5 ml of this solution was added to 3.70 grams of silica (Sipernat 50). 1.15 grams of cross-linked polyvinylpyrrolidone was added as the disintegrant. 218 mg of mix, equivalent to 10 mg of diazepam, was filled into clear No. 2 hard gelatin capsules.

EXAMPLE 4

Digoxin capsules

A 0.25% w/v solution of digoxin was prepared in a solution of 95% Glycofurol: 5% water.

2 ml of solution was added to 1.30 grams of silica (Sipernat 50). 0.35 grams of cross linked polyvinylpyrrolidone was added as the disintegrant. 189 mg of mix, equivalent to 0.25 mg digoxin, was filled into clear No. 2 hard gelatin capsules.

EXAMPLE 5

Capsules of 6-cyano-3,4-dihydro-2,2-dimethyl-trans-4-(2-oxo-1-pyrrolidinyl)-2H-benzo-[b]pyran-3-ol.

The title compound can be formulated into capsules in a manner analogous to that described in Example 4.

EXPERIMENTAL RESULTS AND CONCLUSIONS

Capsules of Example 1 were held in a copper wire twist and placed in 1500 ml of distilled water in a 2 litre round bottom flask, maintained at 37° C.±1° C. The water was stirred for 30 minutes with a USP (1980) paddle stirrer at 60 rpm, 5 ml samples being taken at regular intervals and assayed by UV spectroscopy at 317 nm wavelength. The latter wavelength is known to determine indomethacin in the presence of degradation products.

For comparison, commercially available Indocid 25 mg capsules, (Indocid is a trade mark), were subjected to the same treatment as above.

Indocid capsules were found to release their contents relatively slowly, and only 57% was released within 30 minutes. By contrast, release from the capsules of Example 1 was more rapid and more complete. After 30 mins, about 95% of the contents of the Indomethacin capsules of Example 1, using 25% Synperonic 8 in dimethylisosorbide as liquid carrier, were released.

I claim:

1. A pharmaceutical composition comprising a freely flowable powder, the powder comprising a porous, high absorption silica or silicate having a mean particle size of at least 10 $\mu$m in diameter and having absorbed therein at least 10% by volume of a liquid, anti-hypertensive composition, based on the weight of powder plus liquid; said liquid, pharmacuetically active composition comprising the pharmaceutically active ingredient in a liquid diluent of carrier.

2. A composition according to claim 1 wherein the porous, high absorption silica is a precipitated silica or a xerogel.

3. A composition according to claim 1 wherein the porous high absorption silicate is aluminosilicate or calcium silicate.

4. A composition according to claim 1 wherein the silica or silicate has a mean particle size of from 10 $\mu$m to 1 mm in diameter.

5. A composition according to claim 1 wherein the composition is in unit dosage form.

6. A composition according to claim 5 wherein the unit dosage form is a tablet.

7. A composition according to claim 6 whrein the silica or silicate has a mean particle size of from 50 $\mu$m to 500 $\mu$m in diameter.

8. A composition according to claim 1 wherein the unit dosage form is a capsule.

9. A composition according to claim 8 wherein the silica or silicates has a mean particle size of from 20 $\mu$m to 1 mm in diameter.

10. A composition according to claim 1 wherein the liquid, pharmaceutically active composition comprises a pharmaceutically active ingredient and a liquid diluent or carrier.

11. A composition according to claim 10 wherein the liquid diluent or carrier is a water miscible carrier, an oil, and organic carrier or a semi-solid carrier.

12. A composition according to claim 1 wherein the pharmaceutically active ingredient is 6-cyano-3, 4-dihydro-2,2-dimethy-trans-4-(2-oxo-1-pyrrolidinyl)-2H-benzo-[b ]pyran-3-ol.

* * * * *

UNITED STATES PATENT AND TRADEMARK OFFICE
CERTIFICATE OF CORRECTION

PATENT NO. : 4,719,228

DATED : January 12, 1988

INVENTOR(S) : David Alexander Rawlins

It is certified that error appears in the above-identified patent and that said Letters Patent is hereby corrected as shown below:

In claim 1 at column 4, line 32, change [of] to --or--.

In claim 7 at column 4, line 46, change [whrein] to --wherein--.

In claim 12 at column 4, line 63, change [dimethy] to --dimethyl--.

Signed and Sealed this

Twenty-eighth Day of June, 1988

*Attest:*

DONALD J. QUIGG

*Attesting Officer*          *Commissioner of Patents and Trademarks*